(12) United States Patent
Farnan (10) Patent No.: US 9,717,830 B2
(45) Date of Patent: Aug. 1, 2017

(54) INFLOW CANNULA AND BLOOD FLOW ASSIST SYSTEM

(71) Applicant: CircuLite, Inc., Teaneck, NJ (US)

(72) Inventor: Robert C. Farnan, Fort Lauderdale, FL (US)

(73) Assignee: CircuLite, Inc., Teaneck, NJ (US)

( * ) Notice: Subject to any disclaimer, the term of this patent is extended or adjusted under 35 U.S.C. 154(b) by 0 days.

(21) Appl. No.: 14/924,842

(22) Filed: Oct. 28, 2015

(65) Prior Publication Data

US 2017/0119943 A1 May 4, 2017

(51) Int. Cl.
| | |
|---|---|
| *A61N 1/362* | (2006.01) |
| *A61M 1/10* | (2006.01) |
| *A61M 1/12* | (2006.01) |
| *A61M 25/04* | (2006.01) |
| *A61M 25/09* | (2006.01) |
| *A61M 25/10* | (2013.01) |

(52) U.S. Cl.
CPC .......... *A61M 1/1008* (2014.02); *A61M 1/122* (2014.02); *A61M 25/04* (2013.01); *A61M 25/09* (2013.01); *A61M 25/10* (2013.01)

(58) Field of Classification Search
USPC .......................................................... 600/16
See application file for complete search history.

(56) References Cited

U.S. PATENT DOCUMENTS

| | | |
|---|---|---|
| 4,445,896 A | 5/1984 | Gianturco |
| 5,766,151 A | 6/1998 | Valley et al. |
| 5,814,016 A | 9/1998 | Valley et al. |
| 5,863,366 A | 1/1999 | Snow |
| 6,210,397 B1 | 4/2001 | Aboul-Hosn et al. |
| 6,245,007 B1 | 6/2001 | Bedingham et al. |

(Continued)

FOREIGN PATENT DOCUMENTS

| | | |
|---|---|---|
| EP | 1993640 A2 | 11/2008 |
| WO | 2011059908 A1 | 5/2011 |

(Continued)

OTHER PUBLICATIONS

U.S. Patent and Trademark Office, Office Action in U.S. Appl. No. 14/706,226, Jul. 5, 2016.

(Continued)

*Primary Examiner* — Nicole F Johnson
(74) *Attorney, Agent, or Firm* — Wood Herron & Evans LLP (57) ABSTRACT

A system and method of drawing blood from the heart of a patient. The system includes a blood pump, an outflow cannula, and a flexible cannula assembly. The flexible cannula assembly includes a cannula body, a tip, and first and second anchors. The cannula body includes a proximal end coupled to the inlet of the blood pump, a distal end including a first locking element coupled to the tip. The first anchor has a first plurality of arms and is coupled to the tip and adapted to engage the internal surface of the heart wall. The second anchor includes a second plurality of arms and a second locking element and is slidably positioned on the outer wall of the cannula body and adapted to engage the first locking element of the distal end of the cannula body to couple the second anchor to the external surface of the heart wall.

15 Claims, 10 Drawing Sheets

(56) References Cited

U.S. PATENT DOCUMENTS

| | | |
|---|---|---|
| 6,251,093 B1 | 6/2001 | Valley et al. |
| 6,482,171 B1 | 11/2002 | Corvi et al. |
| 6,533,770 B1 | 3/2003 | Lepulu et al. |
| 6,969,379 B1 | 11/2005 | Aboul-Hosn et al. |
| 8,088,138 B2 | 1/2012 | Pandey |
| 8,157,720 B2 | 4/2012 | Marseille et al. |
| 8,333,727 B2 | 12/2012 | Farnan |
| 8,545,379 B2 | 10/2013 | Marseille et al. |
| 8,768,487 B2 | 7/2014 | Farnan et al. |
| 8,939,882 B2 | 1/2015 | Reichenbach et al. |
| 9,168,352 B2 | 10/2015 | Kelly et al. |
| 2002/0099319 A1 | 7/2002 | Saito et al. |
| 2005/0148997 A1 | 7/2005 | Valley et al. |
| 2006/0235357 A1 | 10/2006 | Woodward et al. |
| 2006/0276681 A1 | 12/2006 | Bolling |
| 2007/0134993 A1 | 6/2007 | Tamez et al. |
| 2007/0173879 A1 | 7/2007 | Pandey |
| 2007/0185430 A1 | 8/2007 | Brugger et al. |
| 2007/0197855 A1 | 8/2007 | Richardson et al. |
| 2007/0197856 A1 | 8/2007 | Gellman et al. |
| 2008/0076959 A1 | 3/2008 | Farnan et al. |
| 2009/0023975 A1 | 1/2009 | Marseille et al. |
| 2009/0082778 A1 | 3/2009 | Beane et al. |
| 2009/0149950 A1 | 6/2009 | Wampler |
| 2009/0182188 A1 | 7/2009 | Marseille et al. |
| 2009/0203957 A1* | 8/2009 | LaRose ............... A61M 1/101 600/18 |
| 2009/0270809 A1 | 10/2009 | Duenas |
| 2010/0249490 A1 | 9/2010 | Farnan |
| 2010/0298625 A1 | 11/2010 | Reichenbach et al. |
| 2011/0066170 A1 | 3/2011 | Farnan |
| 2011/0087063 A1 | 4/2011 | Farnan |
| 2011/0112353 A1 | 5/2011 | Farnan et al. |
| 2011/0118668 A1 | 5/2011 | Farnan et al. |
| 2011/0137234 A1 | 6/2011 | Farnan et al. |
| 2011/0213316 A1 | 9/2011 | Ibrahim et al. |
| 2012/0059212 A1 | 3/2012 | LaRose et al. |
| 2012/0220815 A1 | 8/2012 | Richardson et al. |
| 2012/0296152 A1 | 11/2012 | Reichenbach et al. |
| 2013/0060267 A1 | 3/2013 | Farnan et al. |
| 2013/0158338 A1 | 6/2013 | Kelly et al. |
| 2013/0172661 A1* | 7/2013 | Farnan ............... A61M 1/3653 600/16 |
| 2013/0231521 A1 | 9/2013 | Farnan |
| 2013/0245361 A1 | 9/2013 | Wampler |
| 2014/0005467 A1 | 1/2014 | Farnan et al. |
| 2014/0073837 A1 | 3/2014 | Kerkhoffs et al. |
| 2014/0100430 A1 | 4/2014 | Beane et al. |
| 2014/0200550 A1 | 7/2014 | Farnan et al. |
| 2014/0249357 A1 | 9/2014 | Farnan et al. |
| 2014/0257018 A1 | 9/2014 | Farnan |
| 2014/0275723 A1 | 9/2014 | Fritz, IV et al. |
| 2014/0303427 A1 | 10/2014 | Kerkhoffs et al. |
| 2014/0364880 A1 | 12/2014 | Farnan et al. |
| 2015/0005570 A1 | 1/2015 | Fritz et al. |
| 2015/0224240 A1 | 8/2015 | Farnan et al. |
| 2015/0250933 A1 | 9/2015 | Kerkhoffs et al. |
| 2015/0273124 A1 | 10/2015 | Callaway et al. |
| 2015/0335801 A1* | 11/2015 | Farnan ............... A61M 1/1008 600/16 |
| 2015/0335804 A1 | 11/2015 | Marseille et al. |
| 2016/0082176 A1 | 3/2016 | Kelly et al. |

FOREIGN PATENT DOCUMENTS

| | | |
|---|---|---|
| WO | 2013086408 A2 | 6/2013 |
| WO | 2014062827 A1 | 4/2014 |
| WO | 2015138146 A2 | 9/2014 |
| WO | 2015013666 A1 | 1/2015 |

OTHER PUBLICATIONS

European Patent Office, International Search Report and Written Opinion in PCT Application Serial PCT/US2015/059440, Jul. 20, 2016.

U.S. Patent and Trademark Office, Office Action in U.S. Appl. No. 14/313,270, May 19, 2016.

European Patent Office, International Search Report and Written Opinion in PCT U.S. Appl. No. PCT/US2014/044007, Oct. 15, 2014.

The International Bureau of WIPO, International Preliminary Report on Patentability in PCT Application Serial No. PCT/US2014/044007, Jan. 7, 2016.

U.S. Patent and Trademark Office, International Search Report and Written Opinion in PCT Application Serial No. PCT/US2016/029416, Aug. 25, 2016.

* cited by examiner

INFLOW CANNULA AND BLOOD FLOW ASSIST SYSTEM

TECHNICAL FIELD

The present invention generally relates to systems and methods for assisting with pumping blood from the heart of a patient and improving blood circulation.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right surfaces of the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and into the left ventricle. Finally, the blood is pumped from the left ventricle into the aorta and the vascular network.

For the vast majority of the population, the events associated with the movement of blood happen without circumstance. However, for many people the heart fails to provide adequate pumping capabilities. These heart failures may include congestive heart failure (commonly referred to as heart disease), which is a condition that results in any structural or functional cardiac disorder that impairs the ability of the heart to fill with or pump blood throughout the body. Presently, there is no known cure for heart disease and long-term treatment is limited to a heart transplant. With only a little over 2,000 patients receiving a heart transplant each year, and over 16,600 more on the waiting list for a heart, there is a persisting need for a cure or at the minimum a means of improving the quality of life of those patients on the waiting list.

One such means of bridging the time gap while awaiting a transplant is a circulatory assist system. These systems, originally developed over a decade ago, provide assistance to the heart by way of a mechanical pump. In this way, blood is circulated throughout the vascular network despite the diseased heart tissue. Traditionally, these circulatory assist systems include an implantable or extracorporeal pump, a controller (internal or external), and inflow and outflow tubes connecting the pump to the vascular network. FDA approved circulatory assist systems partially relieve symptoms of breathlessness and fatigue associated with severe heart failure and drastically improve quality of life.

However, the surgical process associated with the circulatory assist system is highly invasive. At the very least the procedure involves a thoracotomy, i.e., the opening of the thoracic cavity between successive ribs to expose the internal organs. More typical is cardiac surgery, generally known as open-heart surgery, where the sternum is cut and split to expose the internal organs. Once the thoracic cavity is accessed, the surgeon must enter the thoracic space and puncture both the pericardium and the myocardial wall. There are great risks and an extensive recovery time associated with the invasive nature of the implantation surgery. As such, some patients with severe symptoms are not healthy enough for surgery to receive a circulatory assist system.

SUMMARY

An exemplary embodiment for a system of drawing blood from the heart of a patient includes a blood pump, an outflow cannula, and a flexible cannula assembly. The blood pump includes an inlet and an outlet. The outflow cannula is adapted to fluidly communicate the outlet of the blood pump to the circulatory system of the patient. The flexible cannula assembly is adapted to extend through a heart wall having internal and external surfaces. The flexible cannula assembly includes a cannula body, a tip and first and second anchors. The cannula body includes a proximal end, a distal end including a first locking element, an inner wall defining a lumen, and an outer wall, the proximal end being coupled to the inlet of the blood pump. The tip is coupled with the distal end of the cannula body. The first anchor includes a first plurality of arms. The first anchor is coupled to the tip and adapted to engage the internal surface of the heart wall and operable to resist movement of the cannula assembly in at least one direction along a lengthwise direction of the cannula body. The second anchor includes a second plurality of arms and a second locking element. The second anchor is slidably positioned on the outer wall of the cannula body and adapted to engage the first locking element of the distal end of the cannula body to couple the second anchor to the external surface of the heart wall.

In another aspect, the invention provides a method of securing a flexible cannula assembly to both internal and external surfaces of a heart wall of a patient. The flexible cannula assembly includes a cannula body including a proximal end, a distal end having a first locking element, an inner wall defining a lumen, an outer wall, and a tip coupled to the distal end of the cannula body. The method includes introducing the tip through the external and internal surfaces of the heart wall, such that the tip is in fluid communication with a first chamber of the heart. The method further includes deploying a first anchor that includes a first plurality of arms. The first anchor is coupled to the tip to secure the flexible cannula assembly to the internal surface of the heart wall. The method further includes moving a second anchor including a second plurality of arms and a second locking element distally towards the external surface of the heart wall. The method further includes coupling the first locking element of the distal end of the cannula body to the second locking element of the second anchor to secure the flexible cannula assembly to the external surface of the heart wall. The method further includes coupling a proximal end of the cannula body to an inlet of a pump. The method further includes operating the pump to draw blood from the first chamber of the heart through the tip and into the lumen of the cannula body.

Various additional objectives, advantages, and features of the invention will be appreciated from a review of the following detailed description of the illustrative embodiments taken in conjunction with the accompanying drawings.

DETAILED DESCRIPTION

Figure 1:
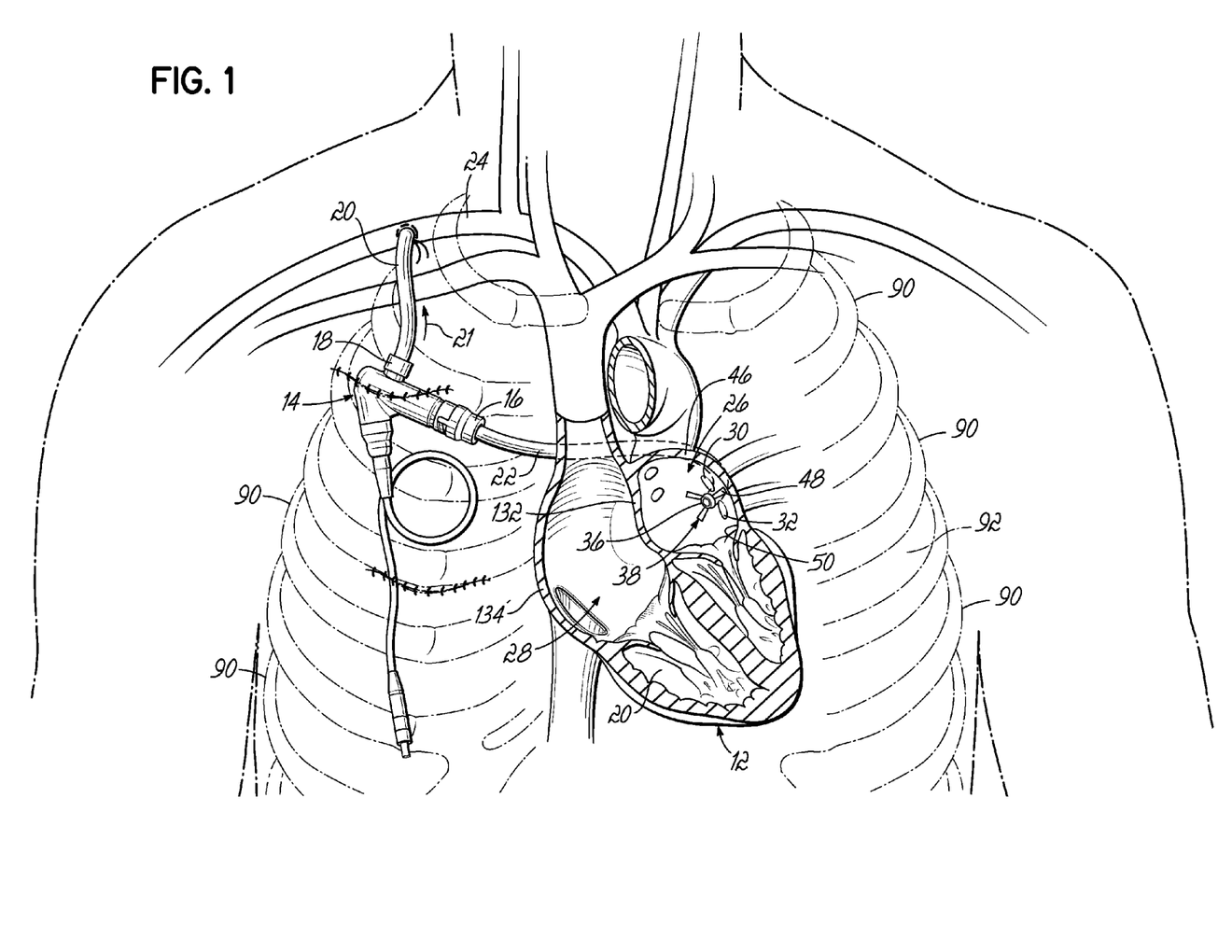
FIG. 1 is a diagrammatic view of a patient with the heart in cross section with the system implanted in the patient according to an embodiment of the present invention.

Referring now to the figures, and to FIG. 1 in particular, the system 10 for drawing blood from the heart 12 of a patient is shown according to various embodiments of the present invention. The system 10 includes a blood pump 14 having an inlet 16 and an outlet 18, an outflow cannula 20, and a flexible cannula assembly 22. The outflow cannula 20 is in fluid communication with the blood pump 14 and the circulatory system of the patient. Specifically, the outflow cannula 20 is in fluid communication with both the outlet 18 of the blood pump 14 and with the right subclavian artery 24 of the patient. Operating the blood pump 14 causes blood to be drawn from the left atrium 26, through the flexible cannula assembly 22, out of the outflow cannula 20 (as shown by arrow 21), and into the right subclavian artery 24.

Figures 2A, 2B:
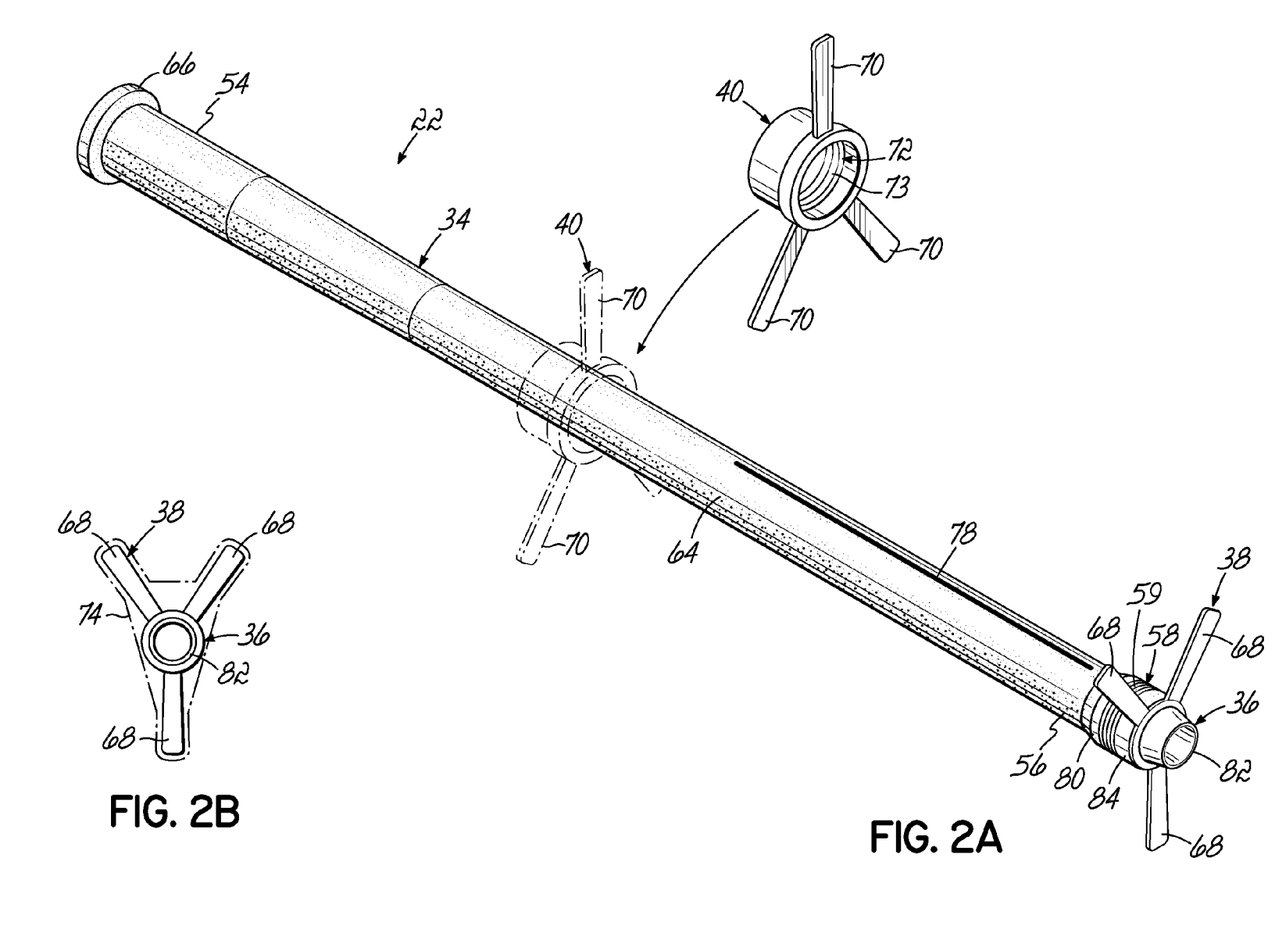
FIG. 2A is a perspective view of the flexible cannula assembly.
FIG. 2B is a front view of an alternative embodiment of the flexible cannula assembly of FIG. 2A, showing details of the distal end thereof.

FIG. 1 shows the flexible cannula assembly 22 in the implanted state, where the flexible cannula assembly 22 is directed into the left atrium 26, behind the right atrium 28, and between the first and second left pulmonary veins 30, 32. The flexible cannula assembly 22 includes a cannula body 34, a tip 36, a first anchor 38, and a second anchor 40 (as shown in FIG. 2). As shown in FIG. 1, and more clearly in the cross-sectional views of FIGS. 4A-4H, the left atrial wall 46 has external and internal surfaces 48, 50. The tip 36 of the flexible cannula assembly 22 is inserted through the external surface 48 of the left atrial wall 46 then through the internal surface 50 of the left atrial wall 46 between first and second left pulmonary veins 30, 32.

Figure 1A:
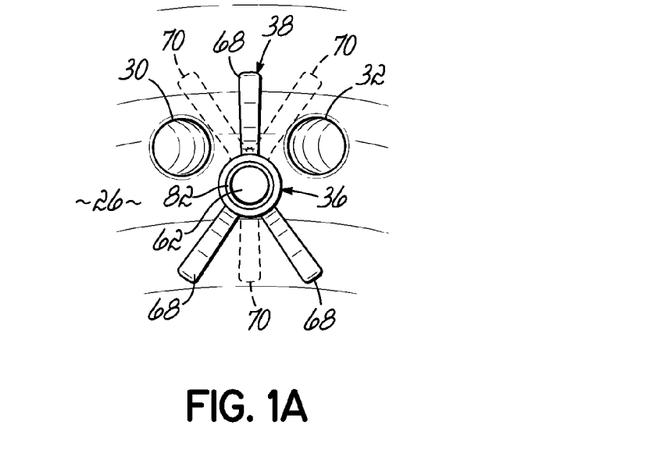
FIG. 1A is a front view of the system implanted in the patient of FIG. 1, showing details of the tip in an exemplary implanted position.

FIG. 1A shows the tip 36 approximately centered between the first and second left pulmonary veins 30, 32. As a result, the center of tip 36 may be less than 1 centimeter away from each of the first and second left pulmonary veins 30, 32. To provide additional space between the access site 52 and the first and second left pulmonary veins 30, 32, the access site 52 may be made more proximal towards the right atrium 28 which will require more resection of the tissue surrounding the heart 12 to clearly see the intersection of the right atrium 28 and the Waterson's Groove. Entering the left atrium 26 in this manner prevents venous obstruction, since the cannula body 34 is generally external to the left atrium 26. This contrasts other methods where the cannula body 34 extends through right atrium 28 where the risks associated with biological sheathing of the cannula body 34 is possible and concerns for embolic events must be considered and prevented.

Figure 3:
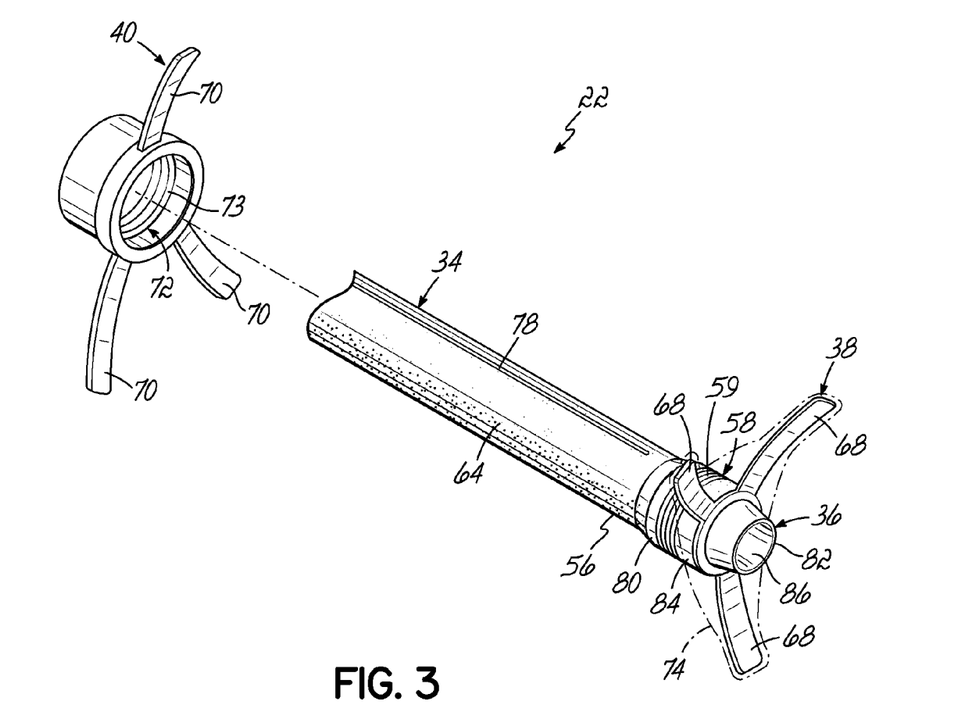
FIG. 3 is a perspective view of the flexible cannula assembly according to another embodiment of the present invention.

FIGS. 2A and 3 show the cannula body 34 as including a proximal end 54, a distal end 56 including a first locking element 58, an inner wall 60 defining a lumen 62 (as shown in FIGS. 4D-4H), and an outer wall 64. The proximal end 54 of the cannula body 34 is coupled to the inlet 16 of the blood pump 14 (as shown in FIG. 1). Likewise, the distal end 56 of the cannula body 34 is coupled with the tip 36. The inner wall 60, defining the lumen 62, extends between the proximal end 54 and distal end 56. The proximal end 54 also includes a lip 66. When implanted, the cannula body 34 has a characteristic "S" shaped bend. The cannula body 34 may be made from any suitable material. One such suitable material is liquid silicone rubber, such as MED-4830, commercially available from Nusil Technology of Carpinteria, Calif.

The cannula body 34 may include an alignment mark 78 along at least a portion of the lengthwise axis 76. FIGS. 2A and 3 each show the alignment mark 78 being a solid line. Alternatively, one skilled in the art will appreciate that the alignment mark 78 may be a dashed line, or a combination of a solid line and a dashed line. When using a combination of lines as the alignment mark 78, the dashed line may be placed diametrically opposite to the solid line. The alignment mark 78 provides a visual communication of the relative rotational positions between the proximal end 54 of the cannula body 34 and the blood pump 14. The alignment may also be radio-opaque. This helps the surgeon precisely position the first and second anchors 38, 40 to avoid obstructing the first and second left pulmonary veins 30, 32.

FIGS. 2A and 3 show perspective views of the flexible cannula assembly 22 including first and second anchors 38, 40. The first anchor 38 includes a first plurality of arms 68, while the second anchor 40 includes a second plurality of arms 70 and a second locking element 72. The first anchor 38 is positioned distally relative to the second anchor 40. The first anchor 38, coupled to the tip 36, engages the internal surface 50 of the left atrial wall 46. As used herein, "coupled" means connected to or integral with. If desired to better accommodate a patient, each arm of the first and second plurality of arms 68, 70 may have a different length. The first anchor 38 prevents movement of the flexible cannula assembly 22 in at least one direction along a lengthwise direction of the cannula body 34. Specifically, the first anchor 38 prevents the flexible cannula assembly 22 from exiting the left atrium 26 of the heart 12.

The second anchor 40 is slidably positioned on the outer wall 64 of the cannula body 34. The second locking element 72 of the second anchor 40 mates with the first locking element 58 of the distal end 56 of the cannula body 34 to couple the second anchor 40 to the external surface 48 of the left atrial wall 46. Specifically as shown, the second teeth 73 of the second locking element 72 are moved distally to mate with first teeth 59 of the first locking element 58 in a ratcheting motion. Alternatively, the first and second teeth 59, 73 may be threaded to couple the second anchor 40 to the external surface 48 of the left atrial wall 46. The mating first and second locking elements 58, 72 prevent relative movement along the lengthwise axis 76 between the first and second anchors 38, 40. The first teeth 59, with six individual teeth shown, allow for multiple locking positions to accommodate varying left atrial wall 46 thicknesses. Alternatively, the second teeth 73 may be comprised of a single receiving element (not shown) that mates with the first teeth 59 of the first locking element 58. The force necessary to mate the first locking element 58 with the second locking element 72 is preferably less than the force to decouple the second locking element 72 from the first locking element 58 for removal. This prevents accidental slippage or removal of second anchor 40. This may be prevented through the shape of the first and second teeth 59, 73 or by other methods known to a person skilled in the art.

Further, as shown in FIG. 3, the second plurality of arms 70 may be curved to better secure the second anchor 40 to the left atrial wall 46. Specifically, the second plurality of arms 70 may be "cupped" such that the ends of the second plurality of arms 70 curve distally toward the external surface 48 of the left atrial wall 46. One arm of the both the first and second plurality of arms 68, 70 may be separated by more than about 120 degrees from the other arms of the first plurality of arms 68. This allows the one arm to straddle, or be placed between, the first and second pulmonary veins 30, 32. This arrangement secures the tip 36, while avoiding any interference with the first and second pulmonary veins 30, 32. While three arms are shown, more or less arms for each of the first and second plurality of arms 68, 70 may be desirable. Further, the first and second anchors 38, 40 may be made of any suitable material such as nickel titanium, also known as nitinol, which has superelastic properties.

FIGS. 2B and 3 show an alternative embodiment having a porous polymeric structure 74 (shown in phantom lines) generally surrounding the first plurality of arms 68 of the first anchor 38 to promote tissue in-growth, where tissue from the heart 12 may grow and embed within the porous polymeric structure to provide greater structural stability and sealing capacity. Alternatively, one skilled in the art will appreciate that that the second plurality of arms 70 of the second anchor 40, or both the first and second plurality of arms 68, 70 of the first and second anchors 38, 40 may be generally covered with the porous polymeric structure 74 to promote tissue in-growth. The porous polymeric structure 74 further stabilizes the tip 36 to prevent migration of the tip 36. Movement of the tip 36 may result in an obstruction of flow through the cannula thereby causing thrombus to form within the blood pump 14 and subsequent stoppage of the blood pump 14.

The tip 36 includes a proximal tip portion 80, a distal tip portion 82, and a tip body 84 extending the length of the tip 36. The tip 36 includes an inner surface 86 defining the lumen 62, which includes certain dimensions that provide advantageous fluid flow. In one embodiment, the tip body 84 is constructed from a titanium alloy, such as TiAl 6Va EL 1, by standard turning, wire electrical discharge machining (EDM), or other machining processes. As shown, the tip 36 has a unitary construction, however if desired, the tip 36 may be comprised of multiple components. The tip 36 may further include one or more barbs 88 on the tip body 84, which provide resistance against the undesired removal of the cannula body 34 from the tip 36.

As shown more clearly in the cross-sectional views of FIGS. 4D-4H, the proximal tip portion 80 and the distal tip portion 82 are generally campanulate (bell-shaped). The campanulate shaped portions of the tip 36 provide fluid flow benefits for the system 10. Specifically, the campanulate shape provides a smoother flow transition, and thus lower pressure losses, as a fluid is moving from the larger heart chamber, into the lumen 62 of the cannula body 34. Furthermore, the campanulate shape reduces the occurrence of turbulence of blood at the tip 36 and in the cannula body 34 when blood is drawn into the lumen 62, thereby increasing the overall efficiency and efficacy of the system 10. Additionally, the tip 36 may be polished in order to remove any imperfections that may cause thrombus. Moreover, the transition between the cannula body 34 and the tip 36 is smooth and free of irregularities that may cause thrombus.

FIGS. 4A-4H show a portion of the method of securing a flexible cannula assembly 22 to both the external and internal surfaces 48, 50 of the left atrial wall 46 of a patient according to one embodiment. The surgeon, before, during, or after readying the system 10, may begin the procedure used in implanting the flexible cannula assembly 22. The method begins with the surgeon making an incision (not shown). Once the incision is made, the surgeon spreads apart the ribs 90 adjacent the incision in order to allow for access to the interior of the thoracic cavity. In one embodiment, the flexible cannula assembly 22 may be implanted using a mini-thoracotomy procedure through the fourth intercostal space 92. For insertion of the flexible cannula assembly 22, a piercing device 94, a delivery sheath 96, and a balloon catheter 98 may be utilized as will be discussed below.

Figure 4A:
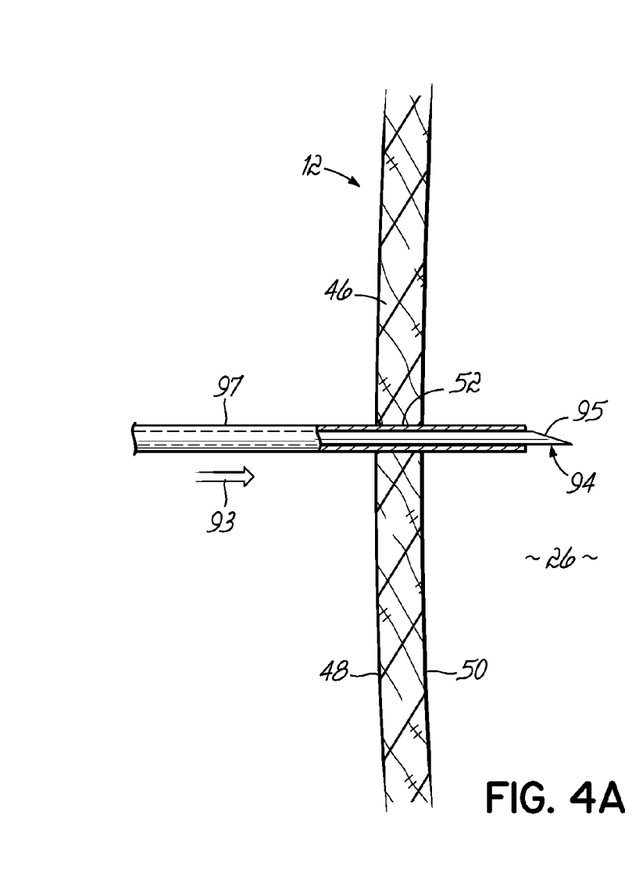
FIG. 4A is a surface cross-sectional view of the piercing device extending through the heart wall.

FIG. 4A shows the piercing device 94 being directed by a surgeon into the thoracic cavity, through the left atrial wall 46, and into the left atrium 26 (as shown by arrow 93). As shown, the piercing device 94 includes an inner piercing stylet 95 that is movable relative to an outer hypotube 97. However, the piercing device 94 may simply be a needle including a lumen and a sharp distal end. Variability in precisely puncturing between the first and second left pulmonary veins 30, 32 may cause future complications. Various features used in this invention, such as for example, the piercing device 94, the delivery sheath 96, the balloon catheter 98, the ring member 100, guidewire 102 are shown and described in U.S. Provisional Patent Application Ser. No. 62/000,788, filed May 20, 2014 and entitled HEART ASSIST SYSTEMS AND METHODS, assigned to the assignee of the present invention, is incorporated herein by reference.

Figure 4B:
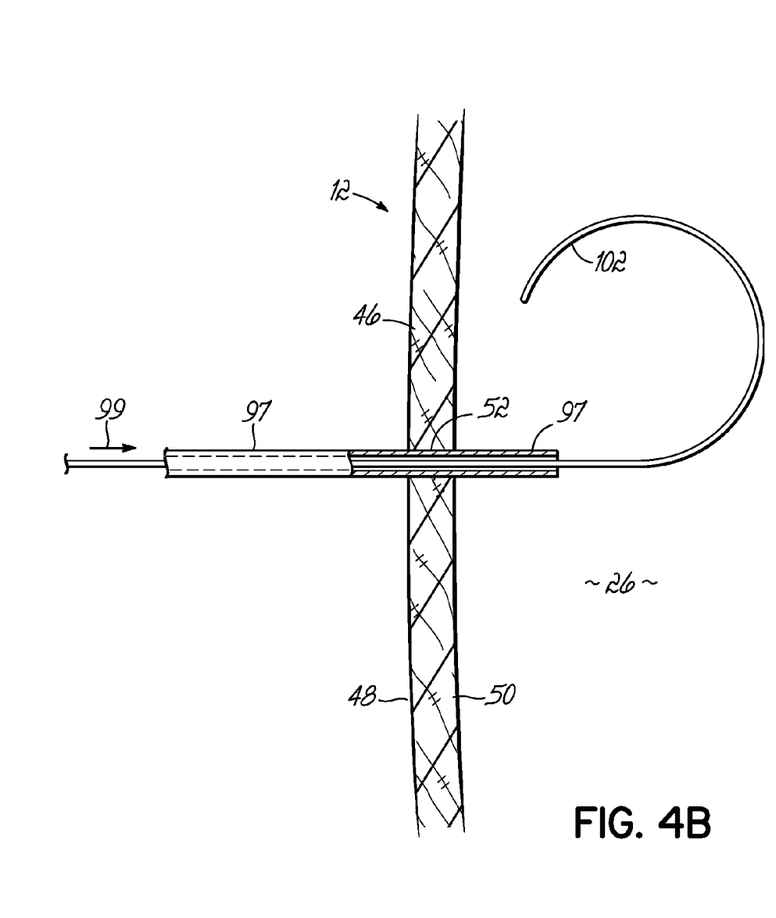
FIG. 4B is a surface cross-sectional view of the guidewire extending through the heart wall.

FIG. 4B shows a guide-element, specifically a guidewire 102, being inserted through the interior of the piercing device 94, as shown by arrow 99. Specifically, the piercing device 94 and guidewire 102 extend through the external and internal surfaces 48, 50 of the left atrial wall 46 and into the left atrium 26. To deliver the flexible cannula assembly 22, a modified Seldinger Technique may be used. Before the specific components can be traversed over the guidewire 102, the components are assembled in order to be directed, as a unit, to the heart 12. Once the guidewire 102 is within the left atrium 26, the piercing device 94 can be retracted and removed, leaving the guidewire 102 within the left atrium 26.

Figure 4C:
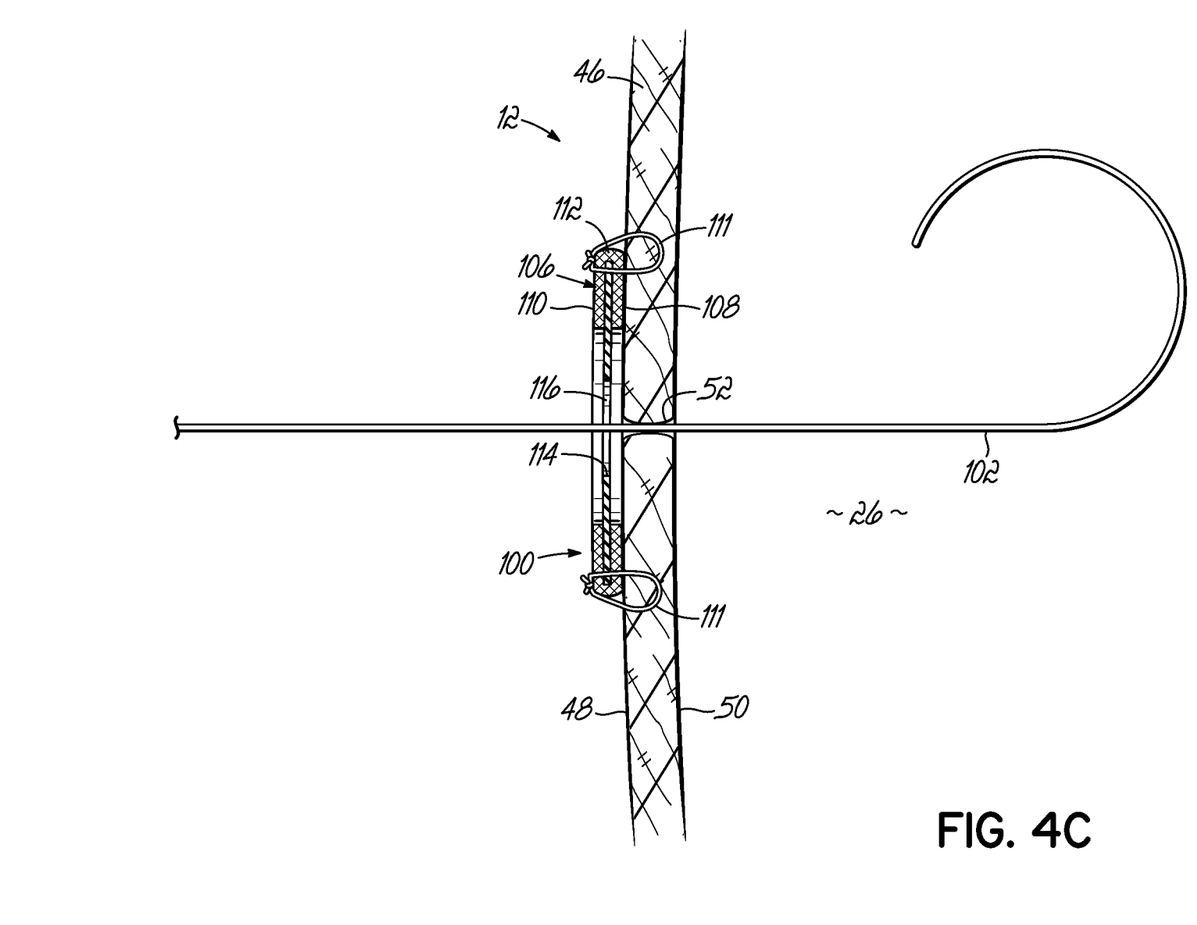
FIG. 4C is a surface cross-sectional view of the ring member attached to the heart wall.

FIG. 4C shows a ring member 100 coupled to the external surface 48. Specifically, the ring member 100 is sewn by sutures 111 to the external surface 48 of the left atrial wall 46 in a generally concentrical position relative to the access site 52 where the guidewire 102 enters the left atrial wall 46. The ring member 100 reinforces the heart tissue surrounding the access site 52 and provides homeostasis between the external surface 48 of the left atrial wall 46 and the cannula body 34. To provide homeostasis, the ring member 100 includes an outer layer 106 that has a generally annular, porous polymeric structure. The outer layer 106 may be one layer of the same polymer or fabric, or may be more than one layer of the same or different polymers or fabrics. The porous polymeric structure aids in tissue in-growth.

The outer layer 106 is generally annular and includes a first surface 108, a second surface 110, an outer edge 112 circumscribing the lengthwise axis 76, and an inner edge 114. The inner edge 114 of the outer layer 106 defines a first aperture 116 circumscribing the lengthwise axis 76. The first aperture 116 includes a cross-sectional dimension, particularly a diameter, which is sized and/or configured to allow the traversal of the system 10. The diameter of the aperture may be smaller than the outer diameter of the delivery sheath 96 resulting in an interference fit with the delivery sheath 96. As described herein, the ring member 100 is preferably coupled to the heart tissue prior to any components of the system 10 being directed into the heart tissue.

Once the guidewire 102 is deployed and the ring member 100 is coupled to the heart 12, the system 10 in the assembled position is traversed over the guidewire 102. More particularly, once the system 10 is assembled, the balloon catheter 98, the flexible cannula assembly 22, and the delivery sheath 96, as a unit, are positioned over the proximal end (not shown) of the guidewire 102 such that guidewire 102 is backloaded into the catheter lumen 118 of balloon catheter 98. Thus, the system 10 is backloaded onto the guidewire 102. Once backloaded onto the guidewire 102, the system 10 is directed into the thoracic cavity through the fourth intercostal space 92. Cannulation of the left atrium 26 through the left atrial wall 46 is accomplished using a modified Seldinger Technique after the ring member 100 is positioned around the access site 52. The flexible cannula assembly 22 is advanced over the guidewire 102 through the left atrial wall 46 into the left atrium 26 with the guidance of a transesophageal echocardiography (TEE).

Figure 4D:
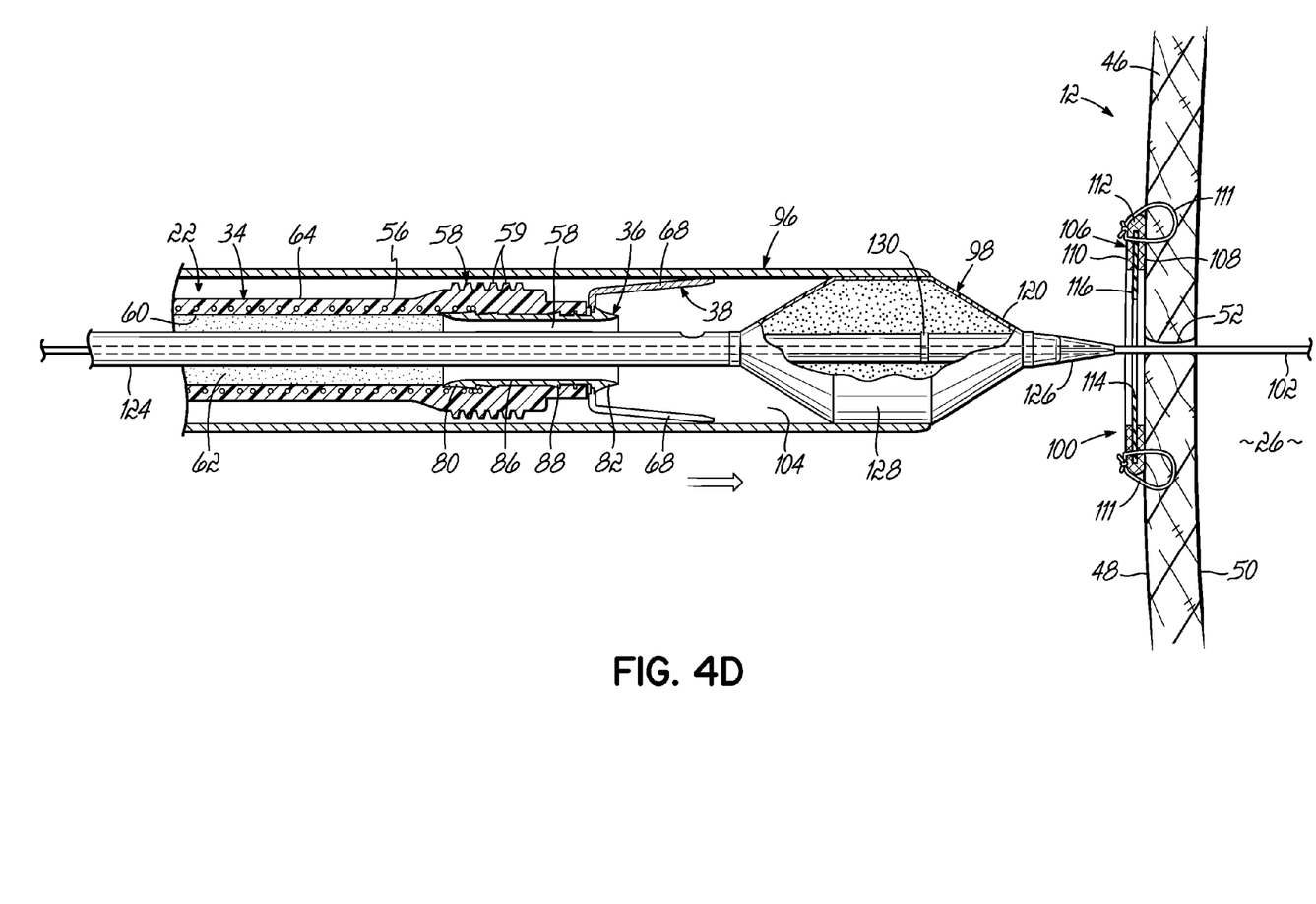
FIG. 4D is a surface cross-sectional view of the guidewire extending through the heart wall.

FIG. 4D shows the balloon catheter 98 for directing the flexible cannula assembly 22 into the heart 12. The balloon catheter 98 includes a distal catheter portion 120, a proximal catheter portion (not shown), and a shaft 124 therebetween. The distal catheter portion 120 of the balloon catheter 98 includes the obturator tip 126 for separating and creating an opening in the tissue through which the system 10 may be inserted. As shown, the guidewire 102 extends from the proximal catheter portion 122 to the distal catheter portion 120 of the balloon catheter 98 such that part of the guidewire 102 extends through the obturator tip 126. The balloon catheter 98, with the flexible cannula assembly 22 and the delivery sheath 96, will follow the guidewire 102 to the left atrial wall 46 to a position generally concentrically relative to the ring member 100. As shown, the distal end 56 of the cannula body 34, and the tip 36, are directed into the sheath lumen 104 of the delivery sheath 96. As the obturator tip 126 is pushed further into the left atrium 26, the obturator tip 126, as well as a proximal cone of the balloon 128, further dilate the heart tissue to create an opening sufficient to allow for the passage of the delivery sheath 96 and the flexible cannula assembly 22. The components are advanced with the guidance of transesophageal echocardiography (TEE).

Figure 4E:
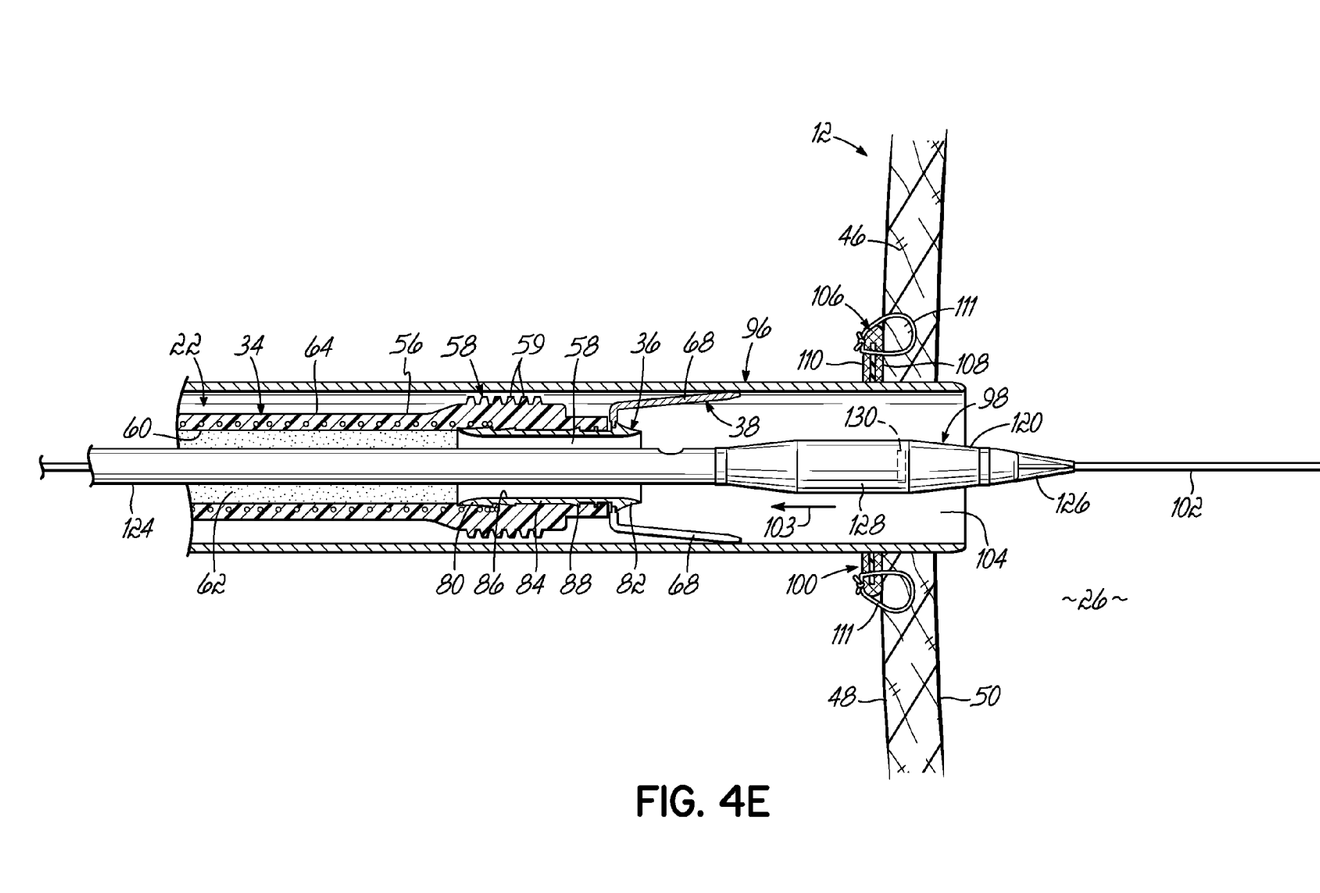
FIG. 4E is a surface cross-sectional view of the delivery sheath extending through the heart wall.

FIG. 4E shows the flexible cannula assembly 22 now having access to the left atrium 26 via the sheath lumen 104 of the delivery sheath 96. In order to deploy the flexible cannula assembly 22, the balloon 128 is deflated and retracted distally. The surgeon may use a marker band 130 (visualized on echocardiography, for example) on each of the tip 36 and the balloon 128 to assist in properly positioning the balloon 128 relative to the tip 36. While not shown, the balloon 128 may then be inflated to engage the inner surface 86 of the tip 36, thus preventing relative movement between the balloon catheter 98 and the tip 36, but still permitting relative movement between the tip 36 and the delivery sheath 96.

With continued reference to FIG. 4E, the balloon catheter 98 is removed before the delivery sheath 96. To remove the balloon catheter 98, the surgeon deflates the balloon catheter 98 enough to allow movement of the balloon catheter 98 within the sheath lumen 104 of the delivery sheath 96. The surgeon then pulls the balloon catheter 98 in the direction of arrow 103 until the balloon catheter 98 exits from the cannula whereby it may be further pulled out of the thoracic cavity through the incision. As shown, the guidewire 102 is removed concurrently with the balloon catheter 98, however, the guidewire 102 may be removed before or after the balloon catheter 98 is removed. Additionally, the balloon catheter 98 may be removed simultaneously with or after the delivery sheath 96.

Figure 4F:
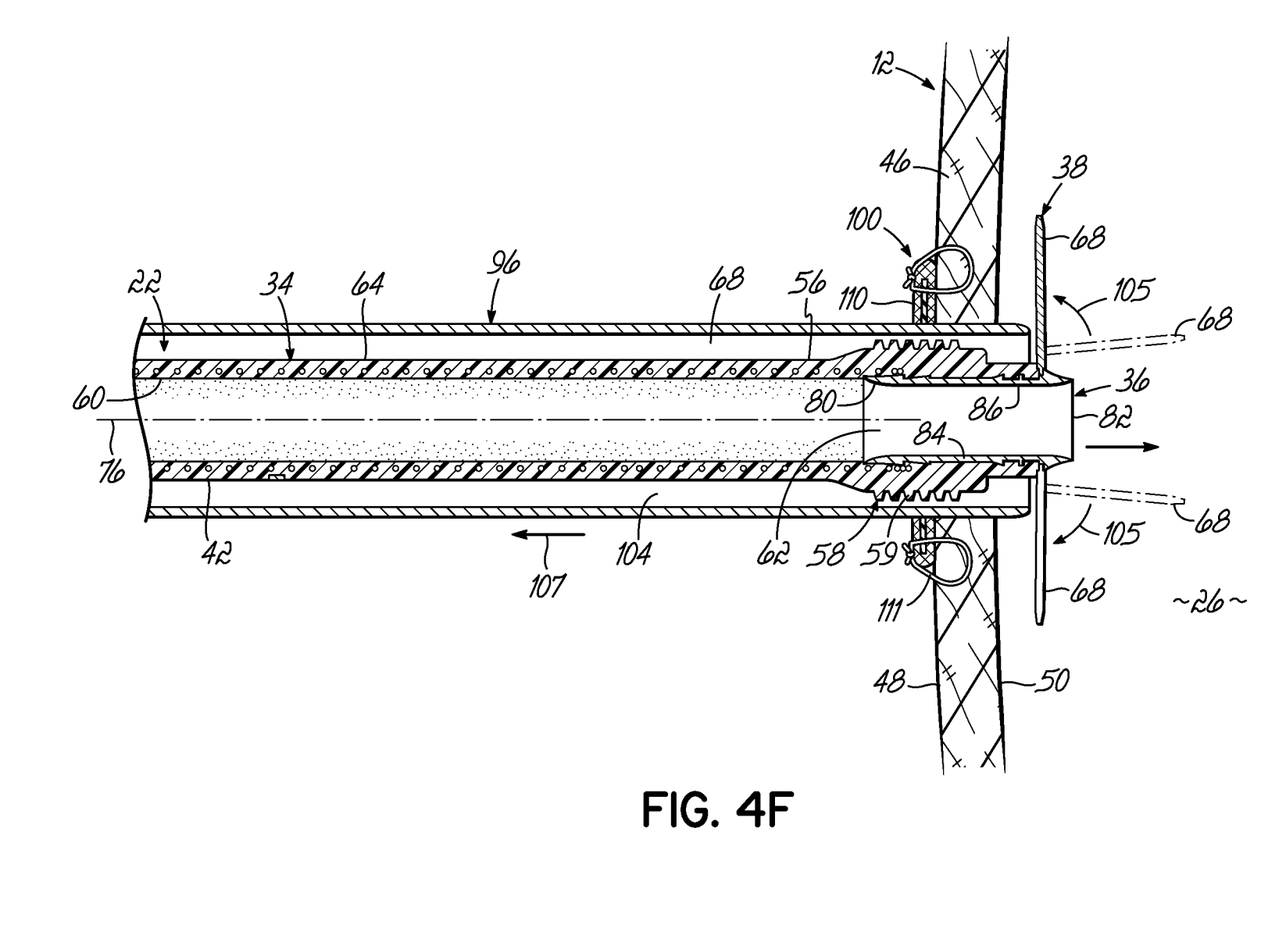
FIG. 4F is a surface cross-sectional view of the first anchor deploying.

FIG. 4F shows the tip 36 extending through the external and internal surfaces 48, 50 of the left atrial wall 46, such that the tip 36 is in fluid communication with the left atrium 26. Specifically, the tip 36 extends beyond the delivery sheath 96, such that the first anchor 38, including the first plurality of arms 68, extends beyond the delivery sheath 96. The first anchor 38 is then deployed from the contracted state (in phantom) to the deployed state (in solid) within the left atrium 26. To deploy the first anchor 38, the first plurality of arms 68 are extended outwardly (as shown by arrow 105) to secure the flexible cannula assembly 22 to the internal surface 50 of the left atrial wall 46. With the first anchor 38 deployed, the delivery sheath 96 can be removed through the thoracic cavity and out through the incision (as shown by arrow 107). Removing the delivery sheath 96 allows the first plurality of arms 68 of the first anchor 38 to contact the internal surface 50 of the left atrial wall 46.

Figure 4G:
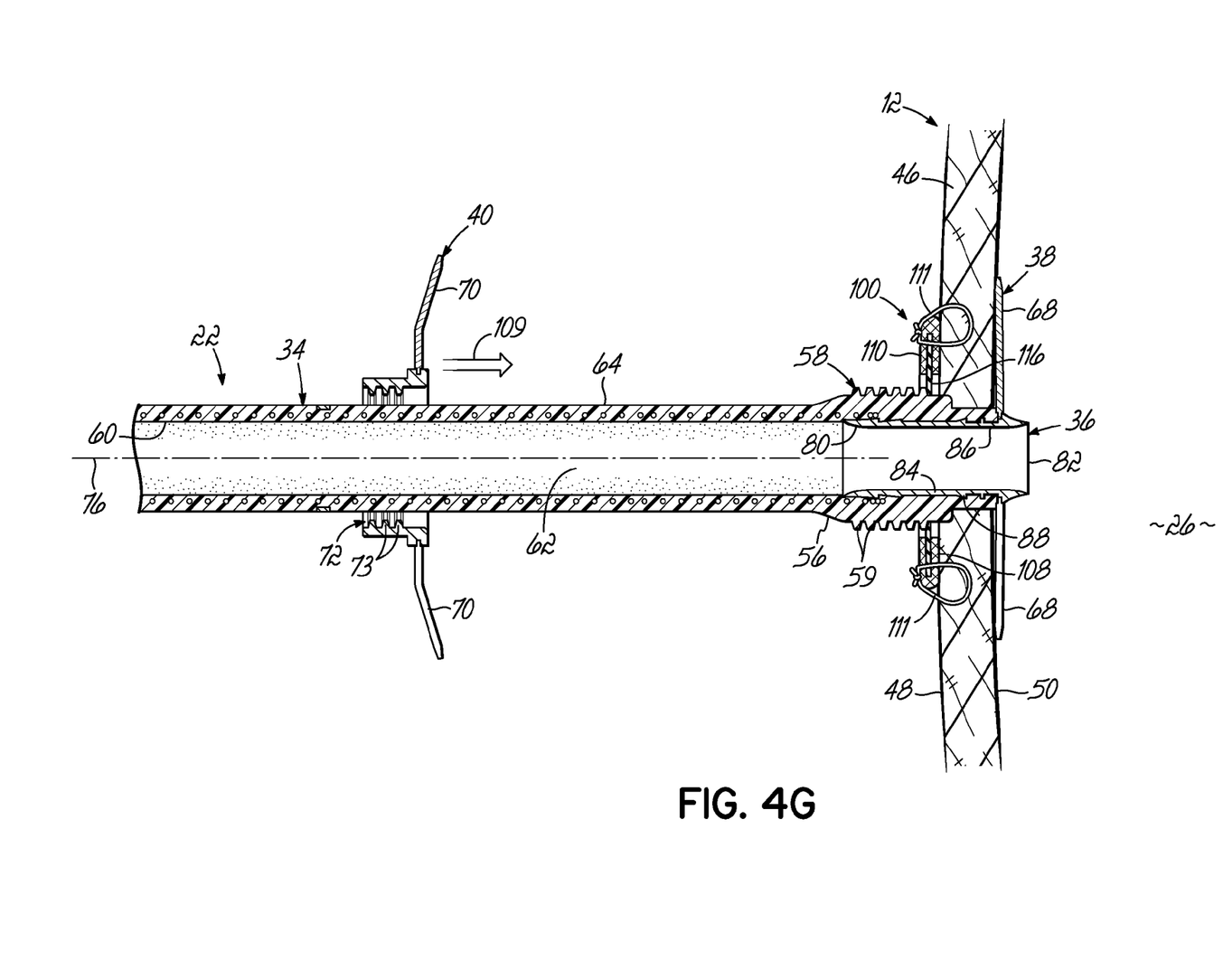
FIG. 4G is a surface cross-sectional view of the second anchor sliding towards the external surface of the heart wall.

FIG. 4G shows the second anchor 40 including the second plurality of arms 70 and a second locking element 72 moving towards the external surface 48 of the left atrium 26 as shown by arrow 109. The second anchor 40 may be positioned over the outer wall 64 of the cannula body 34 using a variety of methods. While not shown, the cannula body 34 may be comprised of multiple sections, allowing the surgeon to place the second anchor 40 around the outer wall 64 of the cannula body 34.

Figure 4H:
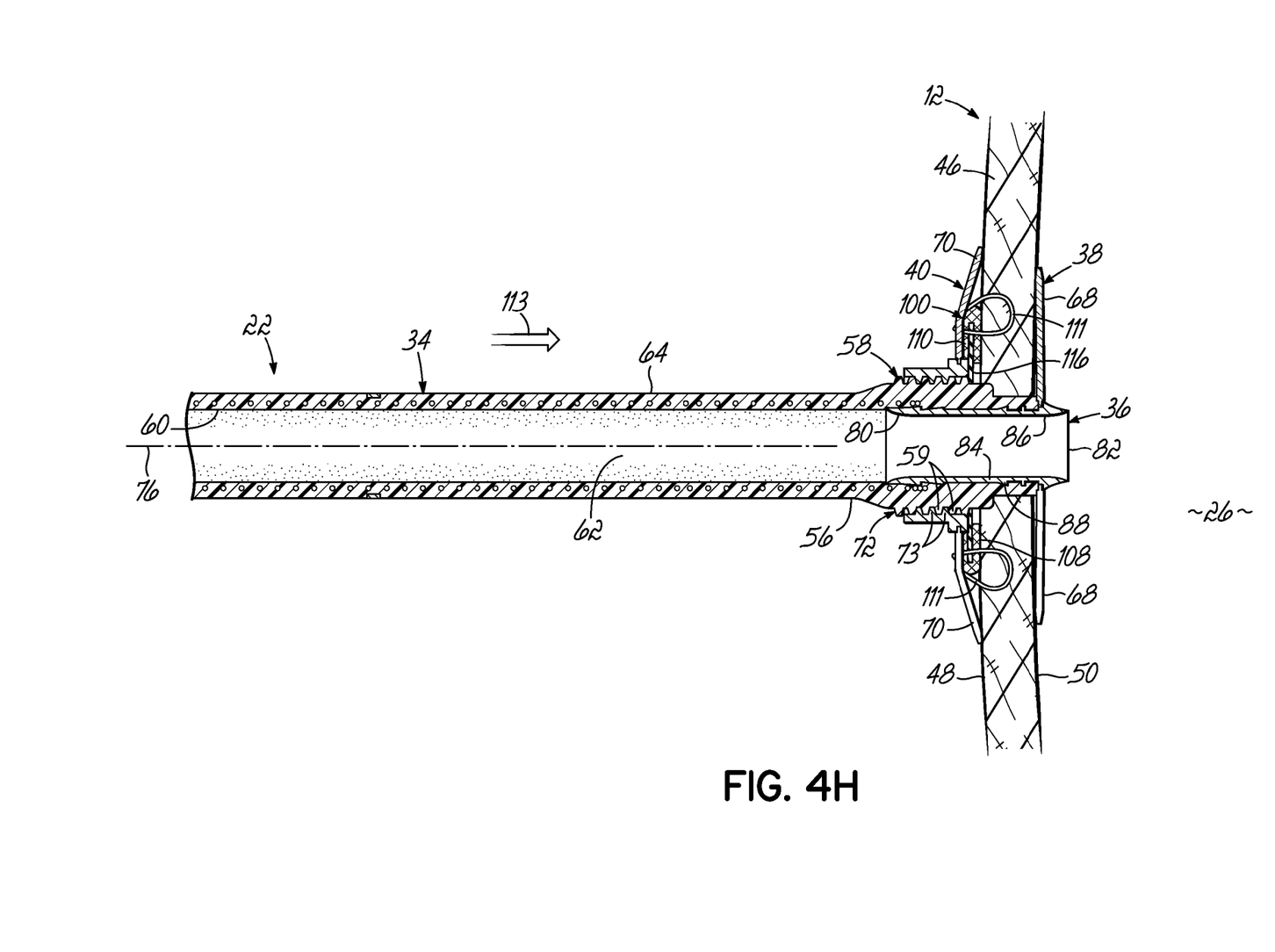
FIG. 4H is a surface cross-sectional view of the second anchor coupling the flexible cannula assembly to the external surface of the heart wall.

FIG. 4H shows the first locking element 58 of the distal end 56 of the cannula body 34 being coupled to the second locking element 72 of the second anchor 40 as shown by arrow 113. The second anchor 40 now deployed and contacting the external surface 48 of the left atrial wall 46 allows the surgeon to successfully "cinch" the atrial tissue securing the flexible cannula assembly 22. Moreover, because visualization within the thoracic cavity may be difficult, many of the steps described herein may be performed with assistance of an imaging technique, such as, for example, echocardiography. Visual confirmation of the position of the tip 36 is desirable to confirm the flexible cannula assembly 22 is in the correct position. Direct visualization may require dissection to expose the Waterson's Groove and the access site 52. In addition to this visual line, transesophageal echocardiography (TEE) is used to confirm that the first and second anchors 38, 40 are positioned between, and not over, the first and second left pulmonary veins 30, 32.

It is desirable that the tip 36 remain in contact with the left atrial wall 46 after the tip 36 enters the left atrium 26. This requires the tip 36 be accurately positioned so that the tip 36 is not inserted too far or not far enough within the left atrium 26. Further, it is desirable that the tip 36 be positioned at a sufficient distance from the first and second left pulmonary veins 30, 32 and opposite anatomical features that make up the left atrium 26. The first and second left pulmonary veins 30, 32 are intended to stay unimpeded and viable for transplant patients. The left atrium 26 being friable and patient-to-patient variation in the thickness of the left atrial wall, possibly caused by variations in the overlying fat pad, make proper placement of the tip 36 more difficult. In the past, these complications have caused the tip 36 to not fully extend into the left atrium 26, but rather reside within the left atrial wall 46 and/or in the overlying fat pad. Making the second anchor 40 adjustable and lockable solves these issues, enabling the second anchor 40 to accommodate the variability of the thickness of the left atrial wall 46.

After the flexible cannula assembly 22 has been implanted, and all assistant devices (balloon catheter 98, delivery sheath 96, guidewire 102 etc.) have been removed, the other components of the system 10 can be implanted. Before the proximal end 54 of the cannula body 34 is connected to the inlet 16 of the blood pump 14, the proximal end 54 may reside within the thoracic cavity, near the fourth, fifth, or sixth intercostal spaces. Thus, the proximal end 54 of the cannula body 34 is directed to the pump pocket, which is a submuscular or subcutaneous space that may be positioned generally at or near the second intercostal space. Specifically, the surgeon may position the blood pump 14 in the pump pocket, or maintain the blood pump 14 externally even after the secondary incision site, that provides access to the pump pocket, is closed. The blood pump 14 may be operably associated with a controller (not shown), which may also be implanted or remain external to the patient. Should the system 10 need to be removed, the left atrial wall 46 may need to be repaired. This contrasts other methods that require repair of both the atrial septum 132 and the right atrial wall 134.

While the present invention has been illustrated by a description of various preferred embodiments and while these embodiments have been described in some detail, this description is not intended to restrict or in any way limit the scope of the appended claims to such details. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A system for drawing blood from the heart of a patient, the system comprising:
   a blood pump including an inlet and an outlet;
   an outflow cannula adapted to fluidly communicate the outlet of the blood pump to the circulatory system of the patient; and
   a flexible cannula assembly adapted to extend through a heart wall having internal and external surfaces, the flexible cannula assembly further comprising:
      a cannula body including a proximal end, a distal end including a first locking element, an inner wall defining a lumen, and an outer wall, the proximal end being coupled to the inlet of the blood pump;
      a tip coupled with the distal end of the cannula body;
      a first anchor including a first plurality of arms, the first anchor being coupled to the tip and adapted to engage the internal surface of the heart wall and operable to resist movement of the cannula assembly in at least one direction along a lengthwise direction of the cannula body; and
      a second anchor including a second plurality of arms and a second locking element, the second anchor positioned on the outer wall of the cannula body, wherein the second locking element slidably engages the first locking element of the distal end of the cannula body to couple the second anchor to the external surface of the heart wall.

2. The system of claim 1, further comprising:
   at least one ring member adapted to be coupled to the external surface and positioned at least partially around the outer wall of the cannula body, the at least one ring member further adapted to provide homeostasis between the external surface of the heart wall and the cannula body.

3. The system of claim 1, wherein the cannula body further comprises:
   an alignment mark located along at least a portion of the lengthwise axis of the cannula body to position at least one of the first and second plurality of arms to avoid obstructing the left pulmonary veins.

4. The system of claim 1, wherein one of the first plurality of arms is separated by more than about 120 degrees from the other arms of the first plurality of arms, and configured to be placed against the internal surface of the heart wall between the left pulmonary veins to avoid obstructing the left pulmonary veins.

5. The system of claim 1, wherein one of the second plurality of arms is separated by more than about 120 degrees from the other arms of the second plurality of arms, and configured to be placed against the external surface of the heart wall between the left pulmonary veins to avoid obstructing the left pulmonary veins.

6. The system of claim 1, wherein the second plurality of arms is curved towards the external surface of the heart wall around the central axis of the cannula body.

7. The system of claim 1, wherein second teeth of the second locking element are configured to engage first teeth of the first locking element in a plurality of locking positions to accommodate varying heart wall thicknesses.

8. The system of claim 1, wherein second teeth of the second locking element are configured to threadably engage first teeth of the first locking element.

9. The system of claim 7, wherein the shape of at least one of the first and second teeth causes the force required to couple the first and second teeth to be less than the force required to decouple the first and second teeth.

10. A method of securing a flexible cannula assembly to both internal and external surfaces of a heart wall of a patient, the flexible cannula assembly including a cannula body including a proximal end, a distal end having a first locking element, an inner wall defining a lumen, and an outer wall, and a tip coupled to the distal end of the cannula body, the method comprising:
   introducing the tip through the external and internal surfaces of the heart wall, such that the tip is in fluid communication with a first chamber of the heart;
   deploying a first anchor including a first plurality of arms, the first anchor being coupled to the tip to secure the flexible cannula assembly to the internal surface of the heart wall;
   moving a second anchor including a second plurality of arms and a second locking element distally towards the external surface of the heart wall;
   coupling the first locking element of the distal end of the cannula body to the second locking element of the second anchor to secure the flexible cannula assembly to the external surface of the heart wall;

coupling a proximal end of the cannula body to an inlet of a blood pump; and operating the blood pump to draw blood from the first chamber of the heart through the tip and into the lumen of the cannula body.

11. The method of claim 10, further comprising:

coupling at least one ring member to the external surface of the heart wall, the at least one ring member defining an aperture sized to create an interference fit with an outer surface of the cannula body.

12. The method of claim 10, wherein moving the second anchor further comprises:

using an alignment mark located on at least a portion of the lengthwise axis of the cannula body to position the second plurality of arms to avoid obstructing a vein.

13. The method of claim 10, wherein deploying the first anchor further comprises:

deploying the first anchor so one arm of the first plurality of arms is separated by more than about 120 degrees from the other arms of the first plurality of arms.

14. The method of claim 10, wherein moving the second anchor further comprises:

deploying the second anchor so one arm of the second plurality of arms is separated by more than about 120 degrees from the other arms of the second plurality of arms.

15. The method of claim 10 wherein coupling the first locking element further comprises:

coupling the first locking element so that the second plurality of arms of the second anchor are curved towards the external surface of the heart wall.

* * * * *